| United States Patent [19] | [11] | 4,086,229 |
|---|---|---|
| Hughes | [45] | Apr. 25, 1978 |

[54] DINITROSYLDIHALO COMPLEXES OF MOLYBDENUM OR TUNGSTEN

[75] Inventor: William B. Hughes, Bartlesville, Okla.

[73] Assignee: Phillips Petroleum Company, Bartlesville, Okla.

[21] Appl. No.: 715,261

[22] Filed: Aug. 18, 1976

[51] Int. Cl.$^2$ .................... C07D 31/24; C07F 11/00
[52] U.S. Cl. .................... 260/270 D; 260/270 PY; 260/429 R; 260/441; 260/446
[58] Field of Search .................... 260/429 R, 441, 446, 260/240 E, 270 D, 270 PY; 252/431 P

[56] References Cited

U.S. PATENT DOCUMENTS

| 3,544,649 | 12/1970 | Dixon et al. .................... 260/270 PY |
| 3,558,518 | 1/1971 | Zuech .................... 252/429 |
| 3,567,731 | 3/1971 | Kubicek et al. .................... 260/270 |
| 3,691,144 | 9/1972 | Zuech .................... 260/270 PY |
| 4,012,399 | 3/1977 | Hechenbleikner et al. ... 260/429 RX |

OTHER PUBLICATIONS

Feltham, Inorganic Chemistry, v1, pp. 116–119, (1964).
Bencze, J. Organometallic Chemistry, v56, pp. 303–306, (1973).
Cotton et al., Inorganic Chemistry, v3, pp. 1609–1612, (1964).
Bencze et al., J. Organometallic Chem., v70, pp. 421–425, (1974).
Hughes et al., Inorganic Chem., v12, pp. 471–473, (1973).
McCleverty et al., J. Chem. Soc. Dalton Trans., pp. 2588–2593, (1972).
Hughes, Advances in Chemistry Series, No. 132, pp. 192–211, (1974).

*Primary Examiner*—Helen M. S. Sneed

[57] ABSTRACT

Dinitrosyldihalo complexes of molybdenum or tungsten are produced from (1) an oxytetrahalide of molybdenum or of tungsten, (2) an alkali metal nitrite, (3) a reducing agent which is metallic iron or a borohydride of sodium, potassium, rubidium, or cesium, (4) a ligand-forming compound, (5) in an aprotic diluent.

33 Claims, No Drawings

DINITROSYLDIHALO COMPLEXES OF MOLYBDENUM OR TUNGSTEN

FIELD OF THE INVENTION

The invention relates to the preparation of dinitrosyldihalo complexes of molybdenum or of tungsten.

BACKGROUND OF THE INVENTION

Dinitrosyldihalo complexes of molybdenum and tungsten are useful as components in catalyst systems. For example, a dinitrosyldihalo complex of molybdenum or tungsten, such as bis(triphenylphosphine)dinitrosyldichloromolybdenum, is a useful component in a catalyst system, such as a homogeneous catalyst system employing the molybdenum or tungsten catalyst component together with an aluminum-containing adjuvant such as methylaluminum sesquichloride, or the like, in a process of olefin disproportionation.

The molybdenum and tungsten complexes heretofore have been prepared by processes such as reacting molybdenum oxytetrachloride with NO and triphenylphosphine, or by reacting dichlorodinitrosylmolybdenum with triphenylphosphine. However, other methods employing more convenient reactants would be desirable, to provide a more useful and economical catalyst system ultimately for such olefin disproportionation reactions.

BRIEF SUMMARY OF THE INVENTION

I have discovered that dinitrosyldihalo complexes of molybdenum and of tungsten can be prepared simply and effectively by reacting a molybdenum or tungsten oxytetrahalide with an alkali metal nitrite, the necessary ligand, a reducing agent which is metallic iron or borohydride of sodium, potassium, rubidium, or cesium and an aprotic diluent.

DETAILED DESCRIPTION OF THE INVENTION

In accordance with my invention, a dinitrosyldihalo complex of molybdenum or of tungsten is prepared by contacting (I) an oxytetrahalide of molybdenum or tungsten, (II) an alkali metal nitrite, (III) a reducing agent which is elemental iron or borohydride of sodium, potassium, rubidium, or cesium, or mixture, (IV) a ligand-forming component and (V) an aprotic diluent.

My procedure provides a quite different method or route in preparing the dinitrosyldihalo complexes of molybdenum or of tungsten as compared to those methods employed heretofore. My process is useful, effective, and much more convenient particularly in that the alkali metal nitrite is much more easily handled, measured, and controlled, than NO or a nitrosyl halide. For examle, the use of NO or a nitrosyl halide frequently results in an overtreatment therewith, which can be undesirable and harmful when the resulting catalyst component subsequently is employed along with an aluminum-containing component in the olefin disproportionation, since excess NO or nitrosyl halide tends to consume some of the aluminum-containing adjuvant. Thus, I can produce the dinitrosyldihalo complexes of molybdenum and tungsten more readily, with better product control, and a more uniform product for use as a catalyst component than has heretofore been possible.

OXYTETRAHALIDE OF MOLYBDENUM OR TUNGSTEN

The (I) molybdenum or tungsten compound employed in accordance with the process of my invention is a molybdenum or tungsten oxytetrahalide.

For convenience, the oxytetrahalides of molybdenum or tungsten can be represented by $MOX_4$ wherein M is molybdenum or tungsten, and X is a halogen and can be any of fluorine, chlorine, bromium, iodine, or combination.

Typical examples of oxytetrahalides of molybdenum or tungsten include molybdenum oxytetrafluoride, molybdenum oxytetrachloride, molybdenum oxytetrabromide, molybdenum oxytetraiodide, molybdenum oxydichloridedibromide, tungsten oxytetrafluoride, tungsten oxytetrachloride, tungsten oxytetrabromide, tungsten oxytetraiodide, tungsten oxybromidetriiodide, and the like, including mixed halo species, and mixtures of any of the species.

ALKALI METAL NITRITES

The (II) alkali metal nitrites employable in accordance with the process of my invention include any of the alkali metal nitrites wherein the alkali metal is lithium, sodium, potassium, rubidium, or cesium. Presently preferred are sodium and potassium nitrite because of their greater availability and low relative cost. Mixtures, of course, of any of the alkali metal nitrites can be employed.

REDUCING AGENT

The (III) reducing agents employed in accordance with the process of my invention are elemental iron or borohydride of sodium, potassium, rubidium, or cesium. Mixtures of the borohydrides, or of elemental iron with one or more of the borohydrides, can be used.

In the case of the elemental iron, it should be in a finely divided state, preferably in the form of an iron powder.

LIGAND-FORMING COMPONENT

The (IV) ligand-forming material or compound employed in accordance with the process of my invention is selected from (A) one or more monodentate ligand-forming compounds selected from tertiary aryl and alkaryl phosphines, arsines, and stibines, and heterocyclic nitrogen-containing compounds of the pyridine, quinoline, or isoquinoline type, and (B) one or more bidentate ligand-forming compounds of the 2,2'-bipyridyl type.

More particularly, the (A) monodentate ligand-forming compounds which are selected from tertiary aryl and alkaryl phosphines, arsines, and stibines can be represented by $R'_3Q$ wherein each $R'$ is an aryl or alkaryl radical having 6 to 12 carbon atoms per radical, and Q is phosphorus, arsenic, or antimony. The alkaryl radical can be an aryl radical with more than one alkyl substituent.

Examples of such ligand-forming compounds include triphenylphosphine, triphenylarsine, triphenylstibine, tri-2-naphthylphosphine, tri-3-biphenylylarsine, diphenyl-o-tolylstibine, tri-p-tolylphosphine, tris(3-ethylphenyl)arsine, tris(4-isopropylphenyl)stibine, tris(3-hexylphenyl)phosphine, tris(4-methyl-1-naphthyl)arsine, tris(2-methyl-5-isopropylphenyl)stibine, tris(pentamethylphenyl)phosphine, and the like, any of these alone, or in admixture, though it is usually preferable to use a single ligand-forming compound for product purity control.

When the monodentate ligand-forming compound is a heterocyclic nitrogen-containing compound of the pyridine, quinoline, or isoquinoline type, such heterocyclic nitrogen-containing compounds can be represented by

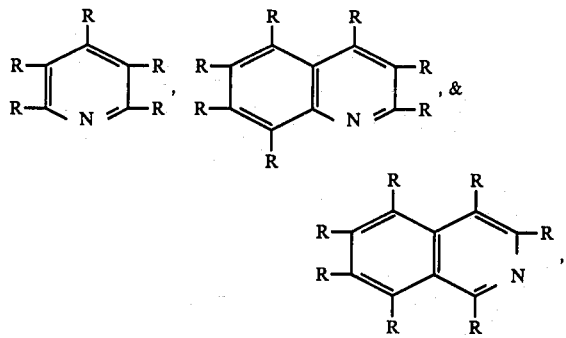

wherein each R is hydrogen or alkyl, such that the total number of carbon atoms in each molecule of such heterocyclic compound is from 5 to 15.

Examples of such monodentate ligand-forming compounds include pyridine, 2-methylpyridine, 4-ethylpyridine, 2-methyl-5-ethylpyridine, 4-isopropylpyridine, 3-hexylpyridine, 4-decylpyridine, pentamethylpyridine, quinoline, 2-methylquinoline, 4-ethyl-6-isopropylquinoline, 8-hexylquinoline, 2,3,4,5,6,7-hexamethylquinoline, isoquinoline, 3-methylisoquinoline, 1-ethyl-4-isobutylisoquinoline, 5-hexylisoquinoline, 1,4,5,6,7,8-hexamethylisoquinoline, alone or in admixture, though it is presently preferred for product control and purity to use a single ligand-forming compound.

When the ligand-forming material is a (B) bidentate ligand-forming compound of the 2,2'-bipyridyl type, such heterocyclic nitrogen-containing compounds can be represented by the formula:

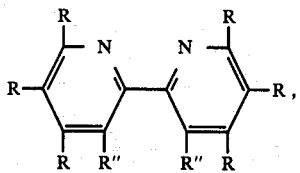

wherein each R and each R" is hydrogen or alkyl, with the proviso that the two R" groups, together, can represent a —CR=CR— group, and such that the total number of carbon atoms per bidentate ligand-forming compound is in the range of 10 to 15.

Examples of such (B) bidentate ligand-forming compounds include 2,2'-bipyridyl, 3-methyl-2,2'-bipyridyl, 4,4'-dimethyl-2,2'-bipyridyl, 5-ethyl-6'-isopropyl-2,2'-bipyridyl, 5-pentyl-2,2'-bipyridyl, 3,3',4,4',5-pentamethyl-2,2'-bipyridyl, 1,10-phenanthroline, 3-methyl-1,10-phenanthroline, 4-isopropyl-1,10-phenanthroline, and the like, alone or in admixture, though normally a single ligand-forming material is to be preferred to maintain control and purity of the complex produced. Of course, it is feasible to use mixtures of any one or all types of the ligand-forming components.

APROTIC DILUENTS

The (V) aprotic diluents employable in accordance with the process of my invention include ethers, chlorinated saturated aliphatic hydrocarbons, and halogenated aromatic hydrocarbons.

The ethers can be cyclic or acyclic, and should contain 4 to 12 carbon atoms per molecule. Typically, these include such as diethyl ether, dibutyl ether, dihexyl ether, dicyclohexyl ether, diphenyl ether, dimethyl ether of ethylene glycol, tetrahydrofuran, and p-dioxane, and the like alone or in admixture.

The chlorinated saturated aliphatic hydrocarbons should contain 1 to 6 carbon atoms per molecule, and include typically such as methylene chloride, chloroform, carbon tetrachloride, ethylene dichloride, butyl chloride, hexyl chloride, and the like, alone or in admixture.

The halogenated aromatic hydrocarbons include the halobenzenes and alkyl-substituted halobenzenes include such as chlorobenzene, bromobenzene, chlorotoluene, bromotoluene, o-dichlorobenzene, and the like, alone or in admixture.

REACTION CONDITIONS

The mole ratio of alkali metal nitrite to molybdenum or tungsten oxytetrahalide can vary over a wide range, so long as it is effective to result in the desired complex. Considered exemplary and suitable is a mole ratio of alkali metal nitrite:oxytetrahalide preferably in the range of about 1:1 to 4:1, more preferably about 1.8:1 to about 2.2:1, and most preferably as close to about 2:1 as convenient.

The ratio of reducing agent to oxytetrahalide also can vary widely, though it is desirable to have a sufficient amount of reducing agent so as to provide desired reactivity of the nitrite. The ratio of reducing agent:oxytetrahalide can be expressed in terms of gram-atoms of elemental iron per mole of oxytetrahalide, or moles of borohydride per mole of oxytetrahalide, and an exemplary ratio in either instance would be in the range of about 1:1 to 5:1, preferably about 2:1 to 3:1.

The ratio of ligand-forming compound to oxytetrahalide also can vary considerably, since if an insufficient ratio is employed reduced productivity of the ultimate product results. However, in general, an exemplary ratio in the case of a monodentate ligand-forming compound would be in the range of about 1:1 to 4:1 mole ratio of ligand-forming component to oxytetrahalide, preferably about 1.8:1 to 2.2:1. In the case of a bidentate ligand-forming component, the mole ratio of bidentate ligand-forming compound to oxytetrahalide also can vary for a similar reason, but generally and exemplarily should be in the range of about 0.5:1 to 2:1, preferably about 0.9:1 to 1.1:1.

The amount of aprotic diluent to be employed can range widely so long as it is sufficient to be suitable and convenient, but generally a range of about 5 to 200, more preferably about 10 to 60, milliliters of aprotic diluent per gram of oxytetrahalide is employed.

The reactions can be conducted at temperatures over a wide range, so long as the temperature is sufficient to provide suitable reactivity of the reagents employed, and so long as temperatures are not too high that would induce undesirable breakdown of components. Typical temperatures would be in the range of about 0° to 200° C., presently preferably about 20° to 150° C. Reaction times can range widely, depending in part on reaction temperatures, as well as the matter of convenience. Typical times would be in the range of a few minutes such as five minutes even to several days, such as four days, though about 1 to 12 hours appears typical. Pressures employed can range widely, and need be sufficient only to substantially maintain the ligand-forming compound and diluent in substantially the liquid phase.

It does not appear that the order of addition of the several components employed in my process is critical, with the exception that the reducing agent must not be added later than substantially at the same time as the addition of the last of the other ingredients. The reaction can be conducted in a batch or continuous process.

The dinitrosyldihalo complexes of molybdenum and tungsten prepared in accordance with the process of my invention can be isolated from the resulting reaction mixture by conventional separation techniques. For example, the dinitrosyldihalo complex produced can be separated from the reaction mixture by distillation of aprotic diluent, extraction of the residual material, and crystallization of the dinitrosyldihalo complex, the crystallization being aided, if desired, by concentration of the extract and/or addition of a diluent which reduces the solubility of the desired product in the extract; by filtration of insoluble material and crystallization of the dinitrosyldihalo complex, the crystallization being aided, if desired, by concentration of the filtrate and/or addition of a diluent which reduces the solubility of the desired product in the filtrate, optionally with the aid of extraction to remove impurities; by filtration of insoluble material, distillation of aprotic diluent from the filtrate, extraction of the distillation residue, and crystallization of the dinitrosyldihalo complex; or by liquid chromatography. The method of product isolation chosen depends in part on the specific substances used as ingredients.

The dinitrosyldihalo complexes of molybdenum and tungsten which can be produced by the process of this invention $MX_2(NO)_2 \cdot L_a$, where M and each X are as defined above, each L is a ligand selected from ligand-forming compounds within the description provided above, and $a$ is an integer of 1 or 2, $a$ being 1 when L is a bidentate ligand and 2 when L is a monodentate ligand.

Examples of some dinitrosyldihalo complexes of molybdenum and tungsten which can be produced by the process of this invention include bis(triphenylphosphine)dinitrosyldichloromolybdenum,
bis(triphenylarsine)dinitrosyldifluorotungsten,
bis(triphenylstibine)dinitrosyldibromomolybdenum,
bis(tri-2-naphthylphosphine)dinitrosyldiiodotungsten,
bis(tri-3-biphenylylarsine)dinitrosyldifluoromolybdenum,
bis(diphenyl-o-tolylstibine)dinitrosyldichlorotungsten,
bis(tri-p-tolylphosphine)dinitrosyldibromomolybdenum,
[tris(3-ethylphenyl)arsine][tris(4-isopropylphenyl)stibine]dinitrosylchlorobromotungsten,
bis[tris(3-hexylphenyl)phosphine]dinitrosyldiiodomolybdenum,
bis[tris(4-methyl-1-naphthyl)arsine]dinitrosyldifluorotungsten,
bis[tris(2-methyl-5-isopropylphenyl)stibine]dinitrosyldichloromolybdenum,
bis[tris(pentamethylphenyl)phosphine]dinitrosyldibromotungsten,
di(pyridine)dinitrosyldichloromolybdenum,
bis(2-methylpyridine)dinitrosyldibromotungsten,
bis(2-methyl-5-ethylpyridine)dinitrosyldiiodomolybdenum,
bis(4-isopropylpyridine)dinitrosyldifluorotungsten,
bis(3-hexylpyridine)dinitrosyldichloromolybdenum,
bis(4-decylpyridine)dinitrosyldibromotungsten,
bis(pentamethylpyridine)dinitrosyldiiodomolybdenum,
di(quinoline)dinitrosyldifluorotungsten,
bis(2-methylquinoline)dinitrosyldichloromolybdenum,
bis(4-ethyl-6-isopropylquinoline)dinitrosyldibromotungsten,
bis(8-hexylquinoline)dinitrosyldiiodomolybdenum,
bis(2,3,4,5,6,7-hexamethylquinoline)dinitrosyldifluorotungsten,
di(isoquinoline)dinitrosyldichloromolybdenum,
bis(3-methylisoquinoline)dinitrosyldibromotungsten,
bis(1-ethyl-4-isobutylisoquinoline)dinitrosyldiiodomolybdenum,
bis(5-hexylisoquinoline)dinitrosyldifluorotungsten,
bis(1,4,5,6,7,8-hexamethylisoquinoline)dinitrosyldichloromolybdenum,
(2,2'-bipyridyl)dinitrosyldibromotungsten,
(3-methyl-2,2'-bipyridyl)dinitrosyldiiodomolybdenum,
(4,4'-dimethyl-2,2'-bipyridyl)dinitrosyldifluorotungsten,
(5-ethyl-6'-isopropyl-2,2'-bipyridyl)dinitrosyldichloromolybdenum,
(5-pentyl-2,2'-bipyridyl)dinitrosyldibromotungsten,
(3,3',4,4',5-pentamethyl-2,2'-bipyridyl)dinitrosyldiiodomolybdenum,
(1,10-phenanthroline)dinitrosyldichloromolybdenum,
(3-methyl-1,10-phenanthroline)dinitrosyldibromotungsten, represented can
(4-isopropyl-1,10-phenanthroline)dinitrosyldifluoromolybdenum, and the like, and mixtures thereof.

EXAMPLES

Examples are provided to assist in an understanding of my invention. Particular species employed, components, ratios, conditions such as temperature and the like, should be considered as exemplary and not limitative of the reasonable scope of my invention in accordance with my disclosure of which the examples are a part.

In the following Runs, the melting points, with decomposition, of the bis(triphenylphosphine)dinitrosyldichloromolybdenum, $MoCl_2(NO)_2(PPh_3)_2$, exhibited considerable variation beyond that which might be expected to result from the degree of sample purity, but this was not surprising in view of differences reported in the published literature "Advances in Chemistry Series, Number 132, Homogeneous Catalysis — II", American Chemical Society, Washington, D.C. (1974), p. 192–211, for the decomposition temperature of this complex.

EXAMPLE I

To a glass vessel equipped with stirrer, condenser, and nitrogen atmosphere were added 1.00 g (0.004 mole) molybdenum oxytetrachloride, 0.56 g (0.008 mole) sodium nitrite, 0.44 g (0.01 gram-atom) iron powder, 2.08 g (0.008 mole) triphenylphosphine, and 40 ml tetrahydrofuran. The mixture was heated to reflux (approximately 65° C), with stirring, and then refluxed with stirring for 3 hours. The resulting mixture was cooled and filtered to give a green-black solution. Approximately one-half of the tetrahydrofuran was evaporated from the green-black solution. To the concentrated solution was added an equal volume of methanol. After refrigeration of the resulting solution, the solid which precipitated was filtered, washed with methanol, and dried to give 0.31 g of greenish brown solid. The greenish brown solid was extracted with hot benzene to give a green solution and an insoluble brown solid. Upon cooling and slight concentration, a yellow-green solid formed in the green solution.

This yellow-green solid was filtered, washed with methanol, and dried to give 0.02 g of $MoCl_2(NO)_2(PPh_3)_2$ having a melting point of 207° C (dec) and an infrared spectrum which was essentially the same as that of an authentic sample of $MoCl_2(NO)_2(PPh_3)_2$ produced by a method known in the art.

The filtrate from the separation of the yellow-green solid was evaporated to dryness slowly over several days to give a green crystalline residue which was washed with methanol and dried to give 0.1 g of impure $MoCl_2(NO)_2(PPh_3)_2$ having a melting point of 242°–245° C (dec). The infrared spectrum of the product melting at 242°–245° C (dec) showed all of the bands in an infrared spectrum of an authentic sample of $MoCl_2(NO)_2(PPh_3)_2$ plus some additional bands. This impure product was recrystallized by dissolving in chloroform, filtering, adding an equal volume of methanol to the filtrate, refrigerating the mixture, and recovering the resulting dark green crystals by filtration. The crystals were washed with methanol and dried to give $MoCl_2(NO)_2(PPh_3)_2$ melting at 228°–230° C (dec) the infrared spectrum of which was essentially the same as that of an authentic sample of $MoCl_2(NO)_2(PPh_3)_2$.

EXAMPLE II

To a glass vessel equipped with stirrer, condenser, and nitrogen atmosphere, were added 1.00 g (0.004 mole) molybdenum oxytetrachloride, 0.44 g (0.01 gram-atom) iron powder, 2.08 g (0.008 mole) triphenylphosphine, and 40 ml tetrahydrofuran. The mixture was stirred for 10 minutes, after which 0.56 g (0.008 mole) sodium nitrite was added. The mixture was heated to reflux (approximately 65° C), with stirring, and then refluxed with stirring for about 2 hours. The resulting mixture was cooled and filtered to give a dark brown solid and a dark brown filtrate.

The solid was washed with tetrahydrofuran. The combined filtrate and washings were taken to dryness under reduced pressure to give a dark brown gummy residue which was extracted with benzene. The benzene-insoluble residue was filtered and then extracted with a mixture of methanol and chloroform. The residual green crystalline solid was filtered, washed with methanol, and dried to give 0.12 g of impure $MoCl_2(NO)_2(PPh_3)_2$ melting at 186°–192° C (dec).

Recrystallization of this product from a mixture of methanol and chloroform gave impure $MoCl_2(NO)_2(PPh_3)_2$ melting at 250°–252° C (dec).

The infrared spectra of the $MoCl_2(NO)_2(PPh_3)_2$ before and after recrystallization were essentially identical, each of the spectra showing all of the bands in an infrared spectrum of an authentic sample of $MoCl_2(NO)_2(PPh_3)_2$ plus some additional bands.

EXAMPLE III

To a glass vessel equipped with stirrer and nitrogen atmosphere were added 1.0 g (0.004 mole) molybdenum oxytetrachloride, 0.6 g (0.008 mole) potassium nitrite, 0.5 g (0.01 gram-atom) iron powder, and 20 ml tetrahydrofuran. The mixture was stirred at room temperature (about 25° C) for 3 hours. Then 2.1 g (0.008 mole) triphenylphosphine was added, and the mixture was allowed to stand for 3 days. Tetrahydrofuran then was allowed to evaporate from the reaction mixture, and the residue was extracted with chloroform to give a dark green solution. The filtered solution was concentrated in a stream of nitrogen. From the concentrated solution was filtered, as green crystals, 0.04 g of $MoCl_2(NO)_2(PPh_3)_2$ melting at 218°–222° C (dec) and having an infrared spectrum essentially the same as that of an authentic sample of $MoCl_2(NO)_2(PPh_3)_2$.

EXAMPLE IV

To a glass vessel equipped with stirrer and nitrogen atmosphere were added 1.0 g (0.004 mole) molybdenum oxytetrachloride, 0.6 g (0.008 mole) potassium nitrite, 0.4 g (0.01 mole) sodium borohydride, and 20 ml tetrahydrofuran. The mixture was stirred at room temperature (about 25° C) for 3 hours. Then 2.1 g (0.008 mole) triphenylphosphine was added and stirring was continued for 3 hours, after which tetrahydrofuran was allowed to evaporate from the brown reaction mixture. The residue was extracted with 20 ml of chloroform, the extract was filtered, a volume of methanol equal to that of the filtrate was added to the filtrate, and the resulting solution was concentrated by evaporation. From the resulting concentrated mixture was filtered, as a green solid melting at 235°–240° C (dec), 0.09 g of $MoCl_2(NO)_2(PPh_3)_2$ containing a small amount of impurity or impurities, as indicated by comparison of its spectrum with that of an authentic sample of this compound. From the filtrate from the separation of this product was obtained, as a second crop of green solid, 0.119 g of $MoCl_2(NO)_2(PPh_3)_2$ melting at 240°–249° C (dec) containing the same impurity or impurities observed in the green solid above melting at 235°–240° C (dec) but present in greater quantity in the second crop, as indicated by their infrared spectra. The green solid melting at 235°–240° C (dec) was recrystallized by dissolving in chloroform, filtering, adding an equal volume of methanol to the filtrate, refrigerating the mixture, and recovering the resulting dark green crystals by filtration. The crystals were washed with methanol and dried to give $MoCl_2(NO_2(PPh_3)_2$ melting at 222°–226° C (dec) the infrared spectrum of which was essentially the same as that of an authentic sample of $MoCl_2(NO)_2(PPh_3)_2$.

The disclosure, including date, illustrate the value and effectiveness of my invention. The examples, the knowledge and background of the field of the invention and general principles of chemistry and the other applicable sciences, have formed the bases from which the broad descriptions of the invention, including the ranges of conditions and the generic groups of operant components, have been developed, which, in turn, have formed the bases for my claims here appended.

I claim:

1. A process for the preparation of dinitrosyldihalo complexes of a metal selected from molybdenum and tungsten which comprises contacting (I) at least one oxytetrahalide of molybdenum or tungsten, (II) at least one alkali metal nitrite, (III) a reducing agent selected from elemental iron, borohydrides of sodium, potassium, rubidium, and cesium, and mixtures, (IV) at least one ligand-forming compound, and (V) at least one aprotic diluent, employing effective ratios of each material, and employing effective conditions of temperature, pressure, and time.

2. The process according to claim 1 wherein said (I) oxytetrahalide of molybdenum or tungsten can be represented by MOX₄ wherein M is molybdenum or tungsten, and each X is a halogen and is individually selected from fluorine, chlorine, bromine, and iodine.

3. The process according to claim 2 wherein said (I) molybdenum or tungsten oxytetrahalide is molybdenum oxytetrafluoride, molybdenum oxytetrachloride, molybdenum oxytetrabromide, molybdenum oxytetraiodide, molybdenum oxydichloridedibromide, tungsten oxytetrafluoride, tungsten oxytetrachloride, tungsten oxytetrabromide, tungsten oxytetraiodide, tungsten oxybromidetriiodide, or mixture.

4. The process according to claim 1 wherein said (II) alkali metal nitrite is the nitrite of lithium, sodium, potassium, rubidium, or cesium, or mixtures thereof.

5. The process according to claim 1 wherein said (III) reducing agent is said elemental iron and is a finely divided elemental iron.

6. The process according to claim 1 wherein said (III) reducing agent is a said borohydride.

7. The process according to claim 1 wherein said (IV) ligand-forming component is (A) at least one monodentate ligand-forming compound selected from the group consisting of tertiary aryl and alkaryl phosphines, arsines, and stibines, and heterocyclic nitrogen-containing compounds of the pyridine-, quinoline-, and isoquinoline-type; (B) at least one bidentate ligand-forming compound of the 2,2'-bipyridyl type; or (C) mixture.

8. The process according to claim 7 wherein said (IV) ligand-forming compound is (A) a said monodentate ligand-forming compound which is heterocyclic nitrogen compound which is a pyridine-type compound, quinoline-type compound, or isoquinoline-type compound.

9. The process according to claim 8 wherein said (IV) monodentate ligand-forming compound is a heterocyclic nitrogen-containing compound wherein said pyridine-type compound, quinoline-type compound, and isoquinoline-type compound can each be represented by the formulae, respectively:

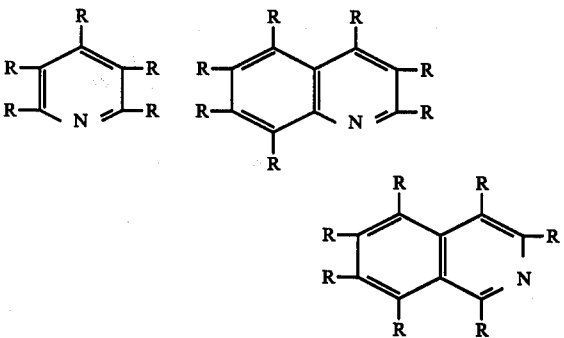

wherein each R is individually selected from hydrogen and alkyl radicals such as the total number of carbon atoms in each such compound is from 5 to 15.

10. The process according to claim 9 wherein said (IV) monodentate ligand-forming compound is a pyridine-type compound selected from the group consisting of pyridine, 2-methylpyridine, 4-ethylpyridine, 2-methyl-5-ethylpyridine, 4-isopropylpyridine, 3-hexylpyridine, 4-decylpyridine, pentamethylpyridine, and mixtures.

11. The process according to claim 9 wherein said (IV) monodentate ligand-forming compound is a quinoline-type compound selected from the group consisting of quinoline, 2-methylquinoline, 4-ethyl-6-isopropylquinoline, 8-hexylquinoline, 2,3,4,5,6,7-hexamethylquinoline, and mixtures.

12. The process according to claim 9 wherein said (IV) monodentate ligand-forming compound is a said isoquinoline-type compound selected from the group consisting of isoquinoline, 3-methylisoquinoline, 1-ethyl-4-isobutylisoquinoline, 5-hexylisoquinoline, 1,4,5,6,7,8-hexamethylisoquinoline, and mixtures.

13. The process according to claim 7 wherein said (IV) ligand-forming compound is (A) a monodentate ligand-forming compound and is a compound of phosphorus, arsenic, or antimony represented by R'₃Q wherein said Q is phosphorus, arsenic, or antimony, and each R' is individually selected from aryl and alkaryl radicals containing 6 to 12 carbon atoms per R' group.

14. The process according to claim 13 wherein said (IV) R'₃Q is selected from the group consisting of triphenylphosphine, triphenylarsine, triphenylstibine, tri-2-naphthylphosphine, tri-3-biphenylylarsine, diphenyl-o-tolylstibine, tri-p-tolylphosphine, tris(3-ethylphenyl)arsine, tris(4-isopropylphenyl)stibine, tris(3-hexylphenyl)phosphine, tris(4-methyl-1-naphthyl)arsine, tris(2-methyl-5-isopropylphenyl)stibine, tris(pentamethylphenyl)phosphine, and mixtures.

15. The process according to claim 7 wherein said (IV) ligand-forming compound is a (B) bidentate ligand-forming compound and is a bipyridyl-type compound represented by the formula:

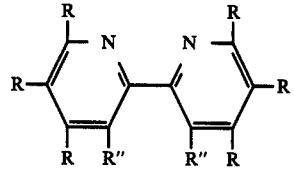

wherein each R and each R'' is hydrogen or alkyl, with the proviso that the two R'' groups together can represent a —CR=CR— group, and such that the total number of carbon atoms per bipyridyl-type compound is 10 to 15.

16. The process according to claim 15 wherein said (IV) compound bi-pyridyl is selected from the group consisting of 2,2'-bipyridyl, 3-methyl-2,2'-bipyridyl, 4,4'-dimethyl-2,2'-bipyridyl, 5-ethyl-6'-isopropyl-2,2'-bipyridyl, 5-pentyl-2,2'-bipyridyl, 3,3',4,4',5-pentamethyl-2,2'-bipyridyl, 4-isopropyl-1,10-phenanthroline, 1,10-phenanthroline, 3-methyl-1,10-phenanthroline, or mixtures.

17. The process according to claim 17 wherein said (IV) ligand-forming compound is triphenylphosphine, triphenylarsine, triphenylstibine, tri-2-naphthylphosphine, tri-3-biphenylylarsine, diphenyl-o-tolylstibine, tri-p-tolylphosphine, tris(3-ethylphenyl)arsine, tris(4-isopropylphenyl)stibine, tris(3-hexylphenyl)phosphine, tris(4-methyl-1-naphthyl)arsine, tris(2-methyl-5-isopropylphenyl)stibine, tris(pentamethylphenyl)-phosphine, pyridine, 2-methylpyridine, 4-ethylpyridine, 2-methyl-5-ethylpyridine, 4-isopropylpyridine, 3-hexylpyridine, 4-decylpyridine, pentamethylpyridine, quinoline, 2-methylquinoline, 4-ethyl-6-isopropylquinoline, 8-hexylquinoline, 2,3,4,5,6,7-hexamethylquinoline, isoquinoline, 3-methylisoquinoline, 1-ethyl-4-isobutylisoquinoline, 5-hexylisoquinoline, 1,4,5,6,7,8-hexamethylisoquinoline, 2,2'-bipyridyl, 3-methyl-2,2'-bipyridyl, 4,4'-dimethyl-2,2'-bipyridyl, 5-ethyl-6'-isopropyl-2,2'-bipyridyl, 5-pentyl-2,2'-bipyridyl, 3,3',4,4',5-pentamethyl-2,2'-bipyridyl, 1,10-phenanthroline, 3-methyl-1,10-phenanthroline, or mixtures.

18. The process according to claim 1 wherein said (V) aprotic diluent is an ether, chlorinated saturated aliphatic hydrocarbon, or halogenated aromatic hydrocarbon.

19. The process according to claim 18 wherein said (IV) aprotic solvent is diethyl ether, dibutyl ether, dihexyl ether, dicyclohexyl ether, diphenyl ether, dimethyl ether of ethylene glycol, tetrahydrofuran, p-dioxane, methylene chloride, chloroform, carbon tetrachloride, ethylene dichloride, butyl chloride, hexyl chloride, or chlorobenzene, bromobenzene, chlorotoluene, bromotoluene, o-dichlorobenzene, or mixture.

20. The process according to claim 7 employing a mole ratio of (II) alkali metal nitrite:(I) oxytetrahalide in the mole ratio range of about 1:1 to 4:1; a mole ratio of (III) reducing agent:(I) oxytetrahalide in the mole ratio range of about 1:1 to 5:1; wherein when said (IV) ligand-forming component is a said (A) monodentate ligand-forming compound, employing a mole ratio of (A) monodentate ligand-forming compound:(I) oxytetrahalide in the mole ratio range of about 1:1 to 4:1, and wherein when said (IV) ligand-forming component is a said (B) bidentate ligand-forming compound, employing a ratio of (B) bidentate ligand-forming compound:(I) oxytetrahalide in the mole ratio range of about 0.5:1 to 2:1; and employing about 5 to 200 milliliters of said (V) aprotic diluent per gram of (I) oxytetrahalide employed.

21. The process according to claim 20 employing a mole ratio of (II) alkali metal nitrite:(I) oxytetrahalide of about 1.8:1 to 2.2:1; a mole ratio of (III) reducing agent:(I) oxytetrahalide of about 2:1 to 3:1; wherein when said (IV) ligand-forming component is a said (A) monodentate ligand-forming compound, employing a ratio of (A) monodentate ligand-forming compound:(I) oxytetrahalide in the mole ratio range of about 1.8:1 to 2.2:1, and wherein when said (IV) ligand-forming component is a said (B) bidentate ligand-forming compound, employing a mole ratio of said (B) bidentate-forming compound:(I) oxytetrahalide of about 0.9:1 to 1.1:1; and employing about 10 to 60 milliliters of said (V) aprotic diluent per gram of (I) oxytetrahalide employed.

22. The process according to claim 21 employing a contacting temperature in the range of about 0° to 200° C.

23. The process according to claim 1 wherein said dinitrosyldihalo complex produced is
bis(triphenylphosphine)dinitrosyldichloromolybdenum,
bis(triphenylstibine)dinitrosyldibromomolybdenum,
bis(tri-3-biphenylylarsine)dinitrosyldifluoromolybdenum,
bis(tri-p-tolylphosphine)dinitrosyldibromomolybdenum,
bis[tris(3-hexylphenyl)phosphine]dinitrosyldiiodomolybdenum,
bis[tris(2-methyl-5-isopropylphenyl)stibine]dinitrosyldichloromolybdenum,
di(pyridine)dinotrosyldichloromolybdenum,
bis(2-methyl-5-ethylpyridine)dinitrosyldiiodomolybdenum,
bis(3-hexylpyridine)dinitrosyldichloromolybdenum,
bis(pentamethylpyridine)dinitrosyldiiodomolybdenum,
bis(2-methylquinoline)dinitrosyldichloromolybdenum,
bis(8-hexylquinoline)dinitrosyldiiodomolybdenum,
di(isoquinoline)dinitrosyldichloromolybdenum,
bis(1-ethyl-4-isobutylisoquinoline)dinitrosyldiiodomolybdenum,
bis(1,4,5,6,7,8-hexamethylisoquinoline)dinitrosyldichloromolybdenum,
(3-methyl-2,2'-bipyridyl)dinitrosyldiiodomolybdenum,
(5-ethyl-6'-isopropyl-2,2'-bipyridyl)dinitrosyldichloromolybdenum,
(3,3',4,4',5-pentamethyl-2,2'-bipyridyl)dinitrosyldiiodomolybdenum,
(1,10-phenanthroline)dinitrosyldichloromolybdenum,
(4-isopropyl-1,10-phenanthroline)dinitrosyldifluoromolybdenum, or mixture.

24. The process according to claim 1 wherein said dinitrosyldihalo complex produced is
bis(triphenylarsine)dinitrosyldifluorotungsten,
bis(tri-2-naphthylphosphine)dinitrosyldiiodotungsten,
bis(diphenyl-o-tolylstibine)dinitrosyldichlorotungsten,
[tris(3-ethylphenyl)arsine][tris(4-isopropylphenyl)stibine]dinitrosylchlorobromotungsten,
bis[tris(4-methyl-1-naphthyl)arsine]dinitrosyldifluorotungsten,
bis[tris(pentamethylphenyl)phosphine]dinitrosyldibromotungsten,
bis(2-methylpyridine)dinitrosyldibromotungsten,
bis(4-isopropylpyridine)dinitrosyldifluorotungsten,
bis(4-decylpyridine)dinitrosyldibromotungsten,
di(quinoline)dinitrosyldifluorotungsten,
bis(4-ethyl-6-isopropylquinoline)dinitrosyldibromotungsten,
bis(2,3,4,5,6,7-hexamethylquinoline)dinitrosyldifluorotungsten,
bis(3-methylisoquinoline)dinitrosyldibromotungsten,
bis(5-hexylisoquinoline)dinitrosyldifluorotungsten,
(2,2'-bipyridyl)dinitrosyldibromotungsten,
(4,4'-dimethyl-2,2'-bipyridyl)dinitrosyldifluorotungsten,
(5-pentyl-2,2'-bipyridyl)dinitrosyldibromotungsten,
(3-methyl-1,10-phenanthroline)dinitrosyldibromotungsten, or mixture.

25. The process according to claim 1 wherein said dinitrosyldihalo complex produced is
bis(triphenylphosphine)dinitrosyldichloromolybdenum,
bis(tri-2-naphthylphosphine)dinitrosyldiiodotungsten,
bis(tri-p-tolylphosphine)dinitrosyldibromomolybdenum,
bis[tris(3-hexylphenyl)phosphine]dinitrosyldiiodomolybdenum,
bis[tris(pentamethylphenyl)phosphine]dinitrosyldibromotungsten, or mixture.

26. The process according to claim 1 wherein said dinitrosyldihalo complex produced is
  bis(triphenylarsine)dinitrosyldifluorotungsten,
  bis(tri-3-biphenylylarsine)dinitrosyldifluoromolybdenum,
  [tris(3-ethylphenyl)arsine][tris(4-isopropylphenyl)stibine]dinitrosylchlorobromotungsten,
  bis[tris(4-methyl-1-naphthyl)arsine]dinitrosyldifluorotungsten, or mixture.

27. The process according to claim 1 wherein said dinitrosyldihalo complex produced is
  bis(triphenylstibine)dinitrosyldibromomolybdenum,
  bis(diphenyl-o-tolylstibine)dinitrosyldichlorotungsten,
  bis[tris(2-methyl-5-isopropylphenyl)stibine]dinitrosyldichloromolybdenum,
  [tris(3-ethylphenyl)arsine][tris(4-isopropylphenyl)stibine]dinitrosylchlorobromotungsten, or mixture.

28. The process according to claim 1 wherein said dinitrosyldihalo complex produced is
  bis(2-methylpyridine)dinitrosyldibromotungsten,
  bis(2-methyl-5-ethylpyridine)dinitrosyldiiodomolybdenum,
  bis(4-isopropylpyridine)dinitrosyldifluorotungsten,
  bis(3-hexylpyridine)dinitrosyldichloromolybdenum,
  bis(4-decylpyridine)dinitrosyldibromotungsten,
  bis(pentamethylpyridine)dinitrosyldiiodomolybdenum, or mixture.

29. The process according to claim 1 wherein said dinitrosyldihalo complex produced is
  di(quinoline)dinitrosyldifluorotungsten,
  bis(2-methylquinoline)dinitrosyldichloromolybdenum,
  bis(4-ethyl-6-isopropylquinoline)dinitrosyldibromotungsten,
  bis(8-hexylquinoline)dinitrosyldiiodomolybdenum,
  bis(2,3,4,5,6,7-hexamethylquinoline)dinitrosyldifluorotungsten, or mixture.

30. The process according to claim 1 wherein said dinitrosyldihalo complex produced is
  di(isoquinoline)dinitrosyldichloromolybdenum,
  bis(3-methylisoquinoline)dinitrosyldibromotungsten,
  bis(1-ethyl-4-isobutylisoquinoline)dinitrosyldiiodomolybdenum,
  bis(5-hexylisoquinoline)dinitrosyldifluorotungsten,
  bis(1,4,5,6,7,8-hexamethylisoquinoline)dinitrosyldichloromolybdenum, or mixture.

31. The process according to claim 1 wherein said dinitrosyldihalo complex produced is
  (2,2'-bipyridyl)dinitrosyldibromotungsten,
  (3-methyl-2,2'-bipyridyl)dinitrosyldiiodomolybdenum,
  (4,4'-dimethyl-2,2'-bipyridyl)dinitrosyldifluorotungsten,
  (5-ethyl-6'-isopropyl-2,2'-bipyridyl)dinitrosyldichooromolybdenum,
  (5-pentyl-2,2'-bipyridyl)dinitrosyldibromotungsten,
  (3,3',4,4'5-pentamethyl-2,2'-bipyridyl)dinitrosyldiiodomolybdenum,
  (1,10-phenanthroline)dinitrosyldichloromolybdenum,
  (3-methyl-1,10-phenanthroline)ditrosyldibromotungsten,
  (4-isopropyl-1,10-phenanthroline)dinitrosyldifluoromolybdenum, or mixture.

32. The process according to claim 22 wherein said (I) oxytetrahalide is molybdenum oxytetrachloride, said (II) alkali metal nitrite is sodium nitrite, said (III) reducing agent is iron powder, said (IV) ligand-forming material is triphenylphosphine, and said (V) aprotic diluent is tetrahydrofuran, and wherein the dinitrosyldihalo complex of molybdenum or tungsten so produced is bis(triphenylphosphine)dinitrosyldichloromolybdenum.

33. The process according to claim 22 wherein said (I) oxytetrahalide is molybdenum oxytetrachloride, said (II) alkali metal nitrite is potassium nitrite, said (III) reducing agent is sodium borohydride, said (IV) ligand-forming material is triphenylphosphine, and said (V) aprotic diluent is tetrahydrofuran, and wherein the dinitrosyldihalo complex of molybdenum or tungsten so produced is bis(triphenylphosphine)dinitrosyldichloromolybdenum.

* * * * *

UNITED STATES PATENT AND TRADEMARK OFFICE
CERTIFICATE OF CORRECTION

PATENT NO. : 4,086,229
DATED : April 25, 1978
INVENTOR(S) : William B. Hughes

It is certified that error appears in the above-identified patent and that said Letters Patent are hereby corrected as shown below:

Col. 10, Claim 16, line 54, after "(IV)" and before "bi-pyridyl" delete "compound".

Col. 10, Cl. 17, line 61, after "claim" and before "wherein" delete "17" and insert --- 7 ---.

Col. 12, Claim 23, line 3, delete "di(pyridine)dinotrosyldichloromolybdenum" and insert --- di(pyridine)dinitrosyldichloromolybdenum ---

Col. 14, Claim 31, line 15, delete "chooromolybdenum" and insert

--- chloromolybdenum ---.

line 17, insert a comma after "4'" to read

--- 3,3',4,4',5-pentamethyl-2,2'-bipyridyl)dinitrosyldiiodomolybdenum, ---.

Signed and Sealed this

Twenty-ninth Day of May 1979

[SEAL]

Attest:

RUTH C. MASON
Attesting Officer

DONALD W. BANNER
Commissioner of Patents and Trademarks